United States Patent
Steenburg et al.

(10) Patent No.: US 11,694,332 B2
(45) Date of Patent: Jul. 4, 2023

(54) ACTIVE BLEEDING MEASUREMENT

(71) Applicant: The Trustees of Indiana University, Indianapolis, IN (US)

(72) Inventors: Scott David Steenburg, Zionsville, IN (US); William J. Borror, Houston, TX (US)

(73) Assignee: The Trustees of Indiana University, Bloomington, IN (US)

( * ) Notice: Subject to any disclaimer, the term of this patent is extended or adjusted under 35 U.S.C. 154(b) by 89 days.

(21) Appl. No.: 16/723,447

(22) Filed: Dec. 20, 2019

(65) Prior Publication Data

US 2020/0219263 A1    Jul. 9, 2020

Related U.S. Application Data

(60) Provisional application No. 62/783,724, filed on Dec. 21, 2018.

(51) Int. Cl.
| | |
|---|---|
| *G06T 7/00* | (2017.01) |
| *A61B 6/00* | (2006.01) |
| *G06T 7/62* | (2017.01) |
| *G16H 50/20* | (2018.01) |

(52) U.S. Cl.
CPC ............ *G06T 7/0016* (2013.01); *A61B 6/504* (2013.01); *G06T 7/62* (2017.01); *G16H 50/20* (2018.01); *G06T 2207/10081* (2013.01); *G06T 2207/30104* (2013.01); *G06T 2207/30196* (2013.01)

(58) Field of Classification Search
CPC ...... G06T 7/0016; G06T 7/62; G06T 2207/30196; G06T 2207/30104; G06T 2207/10081; A61B 6/504; A61B 6/5235; A61B 6/03; A61B 6/5217; G16H 50/20; G16H 20/13; G16H 20/40; G16H 50/30; G16H 30/20; G16H 30/40
See application file for complete search history.

(56) References Cited

U.S. PATENT DOCUMENTS

| | | | | |
|---|---|---|---|---|
| 5,614,204 | A | * | 3/1997 | Cochrum ......... A61B 17/12186 128/DIG. 22 |
| 7,684,600 | B2 | * | 3/2010 | Wang ..................... A61B 6/032 600/407 |
| 2018/0078232 | A1 | * | 3/2018 | Silbert .................. G06T 7/0016 |
| 2019/0267132 | A1 | * | 8/2019 | Fuchigami ............. G06T 11/60 |

(Continued)

OTHER PUBLICATIONS

Borror "Abdominopelvic bleed rate on admission CT correlates with mortality and transfusion needs in the setting of blunt pelvic fractures: a single institution pilot study" Emergency Radiology (Year: 2019).*

(Continued)

*Primary Examiner* — Molly Wilburn
(74) *Attorney, Agent, or Firm* — Faegre Drinker Biddle & Reath LLP

(57) ABSTRACT

A method of treating a human patient identified as having an injury to a body region includes receiving CT images, where the CT images were generated by performing a CT angiography of an injured body region of the human patient. The method further includes determining, based on the CT images, a total volumetric rate of active bleeding in the injured body region; and recommending at least one treatment approach for the human patient based on the total volumetric rate of active bleeding.

19 Claims, 6 Drawing Sheets

(56) References Cited

U.S. PATENT DOCUMENTS

| | | | |
|---|---|---|---|
| 2020/0051246 A1* | 2/2020 | Carmi | G06T 7/0016 |
| 2020/0082525 A1* | 3/2020 | Xu | A61B 5/02042 |
| 2020/0219263 A1* | 7/2020 | Steenburg | G16H 20/13 |

OTHER PUBLICATIONS

Christopher E. White, Joseph R. Hsu, John B. Holcomb, Haemodynamically unstable pelvic fractures, Journey, Int. J. Care Injured 40 (2009), pp. 1023-1030.

Jennifer Uyeda, Stephan W. Anderson, Jennifer Kertesz, Jorge A. Soto, Pelvic CT angiography: application to blunt trauma using 64M DCT, Emerg Radiol (2010) 17:131-137.

Chih-Yuan Fu, MD, et al. Computed tomography angiography provides limited benefit in the evaluation of patients with pelvic fractures, American Journal of Emergency Medicine 32 (2014), pp. 1220-1224.

C. Craig Blackmore, MD, et al. Assessment of Volume of Hemorrhage and Outcome From Pelvic Fracture, Arch Surg., vol. 138, May 2003; 6 pages.

C. Craig Blackmore, MD, et al. Predicting Major Hemorrhage in Patients with Pelvic Fracture, The Journal of Trauma Injury, Infection, and Critical Care, Aug. 2006; 7 pages.

Samir A. Dalal, MD, Pelvic Fracture in Multiple Trauma: Classification by Mechanism is Key to Pattern of Organ Injury, Resuscitative Requirements, and Outcome, The Journal of Trauma, vol. 29, No. 7; 22 pages.

Brian J. Eastridge, MD, Adam Starr, MD, Joseph P. Minei, MD, Grant E. O'Keefe, MD, The Importance of Fracture Pattern in Guiding Therapeutic Decision-Making in Patients with Hemorrhage Shock and Pelvic Ring Disruptions, The Journal of Trauma Injury, Infection, and Critical Care, Sep. 2002; 4 pages.

Adam J. Starr, et al. Pelvic Ring Disruptions: Prediction of Associated Injuries, Transfusion Requirement, Pelvic Arteriography, Complications, and Mortality, Journal of Orthopaedic Trauma, vol. 16, No. 8; pp. 553-561.

Jeremy W.R. Young MD, Andrew R. Burgess MD, Robert J. Brumback MD, Attila Poka MD, Pelvic Fractures: Value of Plain Radiography in Early Assessment and Management, Musculoskeletal Radiology 1986, 160:445-451.

Ashoke K. Sathy, MD, et al., The Effect of Pelvic Fracture on Mortality After Trauma: An Analysis of 63,000 Trauma Patients, The Journal of Bone and Joint Surgery, 2009, 91:2803-10.

Mark E. Elzik, Douglas R. Dirschl, Laurence E. Dahners, Correlation of Transfusion Volume to Change in Hematocrit, American Journal of Hematology, (2006) 81:145-146.

Greg Gaski MD, Travis Frantz BS, Scott Steenburg MD, Teresa Bell PHD, Todd McKinley MD, Large-magnitude Pelvic and Retroperitoneal Tissue Damage Predicts Organ Failure, Clinical Orthopaedics and Related Research (2016, 474:140-1416.

Travis L. Frantz MD, et al., Tissue damage volume predicts organ dysfunction and inflammation after injury, Journal of Surgical Research 202 (2016) 188-195.

David Dreizin, et al. Volumetric analysis of pelvic hematomas after blunt trauma using semi-automated seeded region growing segmentation: a method validation study, Abdominal Radiology (2016) 41:2203-2208.

* cited by examiner

ACTIVE BLEEDING MEASUREMENT

CROSS-REFERENCE TO RELATED APPLICATIONS

This application claims priority to U.S. Provisional Application No. 62/783,724, filed Dec. 21, 2018, entitled "BLEED RATE ON ADMISSION CT CORRELATION WITH MORTALITY AND TRANSFUSION," which is hereby incorporated by reference in its entirety for all purposes.

STATEMENT REGARDING FEDERALLY SPONSORED RESEARCH OR DEVELOPMENT

This invention was made with government support under grant TR001108 awarded by National Institutes of Health. The government has certain rights in the invention.

BACKGROUND

Blunt and penetrating trauma are significant sources of morbidity and mortality in trauma patients. In patients who are stable, imaging evaluation with computed tomography (CT) is frequently performed to identify injuries that are clinically occult. Previous studies have shown that CT can aid in the detection and characterization of injuries that otherwise may have eluded detection. In addition, CT has the ability to identify active bleeding from, and has been shown to be an independent predictor of the failure of non-operative management. In short, imaging of acute trauma patients is common and helps guide the clinician towards any one of several management and treatment pathways, especially when there are signs of internal bleeding. This is particular true with respect to injuries to the organs (such as the liver, spleen and kidneys) and bony pelvis.

Pelvic fractures are associated with substantial morbidity and up to a 40% mortality rate in trauma patients with pelvic hemorrhage and hemodynamic instability. Death from hemorrhage most often occurs in the first 24 h, making rapid diagnosis and treatment critical.

Initial evaluation of patients with pelvic fractures is challenging because of difficulties associated with determining an appropriate intervention and determining urgency. Multiphasic image acquisition is quick, noninvasive and can detect active extravasation of blood. Computed tomography (CT) angiography is used as part of the initial evaluation in patients with pelvic fractures where bleeding is suspected. A need exists for an improved method that results in more accurate determinations of appropriate intervention and urgency.

SUMMARY

Embodiments of the method described herein are used for treating a human patient identified as having an injury to a body region. The method may include the steps of acquiring medical image data, such as by performing or having performed a CT angiography of an injured body region of the human patient, determining or having determined a total volumetric rate of active bleeding in the injured body region; and, selecting or having selected at least one treatment approach for the human patient based on the total volumetric rate of active bleeding in the injured body region of the human patient.

In embodiments, the method treats a human patient identified as having a pelvic injury. The method may include the steps of acquiring medical image data, such as by performing or having performed a CT angiography of an abdomen and a pelvis of the human patient, determining or having determined a total volumetric rate of active abdominopelvic bleeding; and, selecting or having selected at least one treatment approach for the human patient based on the total volumetric rate of active abdominopelvic bleeding of the human patient.

Embodiments include a method of treating a human patient identified as having an injury to a body region. Embodiments of the method include receiving CT images, where the CT images were generated by performing a CT angiography of an injured body region of the human patient; determining, based on the CT images, a total volumetric rate of active bleeding in the injured body region; and recommending at least one treatment approach for the human patient based on the total volumetric rate of active bleeding.

Embodiments include a method of treating a human patient identified as having a pelvic injury. Embodiments of the method include receiving CT images, where the CT images were generated by performing a CT angiography of an abdomen and a pelvis of the human patient; determining, based on the CT images, a total volumetric rate of active abdominopelvic bleeding; and recommending at least one treatment approach for the human patient based on the total volumetric rate of active abdominopelvic bleeding.

Embodiments include one or more computer-readable media having embodied thereon computer-executable instructions that, when executed by a processor, cause the processor to perform a method of treating a human patient identified as having an injury to a body region. Embodiments of the method include receiving CT images, where the CT images were generated by performing a CT angiography of an injured body region of the human patient; identifying a trigger event, the trigger event comprising at least one of receiving an input from a clinician and detecting a trigger feature in the CT images; determining, in response to identifying the trigger event and based on the CT images, a total volumetric rate of active bleeding in the injured body region; and recommending at least one treatment approach for the human patient based on the total volumetric rate of active bleeding.

In an embodiment, a total volumetric rate of active abdominopelvic bleeding less than 20 cc/min indicates a lower risk for mortality and a total volumetric rate of active abdominopelvic bleeding greater than 20 cc/min indicates a higher risk for mortality.

In a further embodiment, the human patient identified as having a pelvic injury is further identified as having a pelvic fracture and active abdominopelvic bleeding.

In an additional embodiment, active bleeding is contrast extravasation seen on the CT scan.

In another embodiment the treatment approach is selected from the group consisting of embolization, blood transfusion, pelvic packing, or pelvic ring stabilization and/or combinations thereof.

In an additional embodiment, the computed tomography scanner is a dual source CT scanner such as a Siemens SOMATOM Force scanner or a Siemens SOMATOM Drive scanner.

In a further embodiment, the computed tomography scanner is a single source CT scanner such as a Siemens SOMATOM Edge Plus scanner.

In yet another embodiment, the computed tomography scanner is a Philips Ingenuity scanner.

In a further embodiment, the CT angiography of the abdomen and pelvis of the human patient is automated.

In yet another embodiment, the CT angiography is a dual-phase (arterial and parenchymal phases) CT of the abdomen and pelvis.

In an embodiment, the CT angiography is a triple-phase (arterial, parenchymal and excretory phases) CT of the abdomen and pelvis.

The retroperitoneum includes hematoma originating from a pelvic fracture and extending into the retroperitoneal space up to the level of the lower pole of the kidney.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
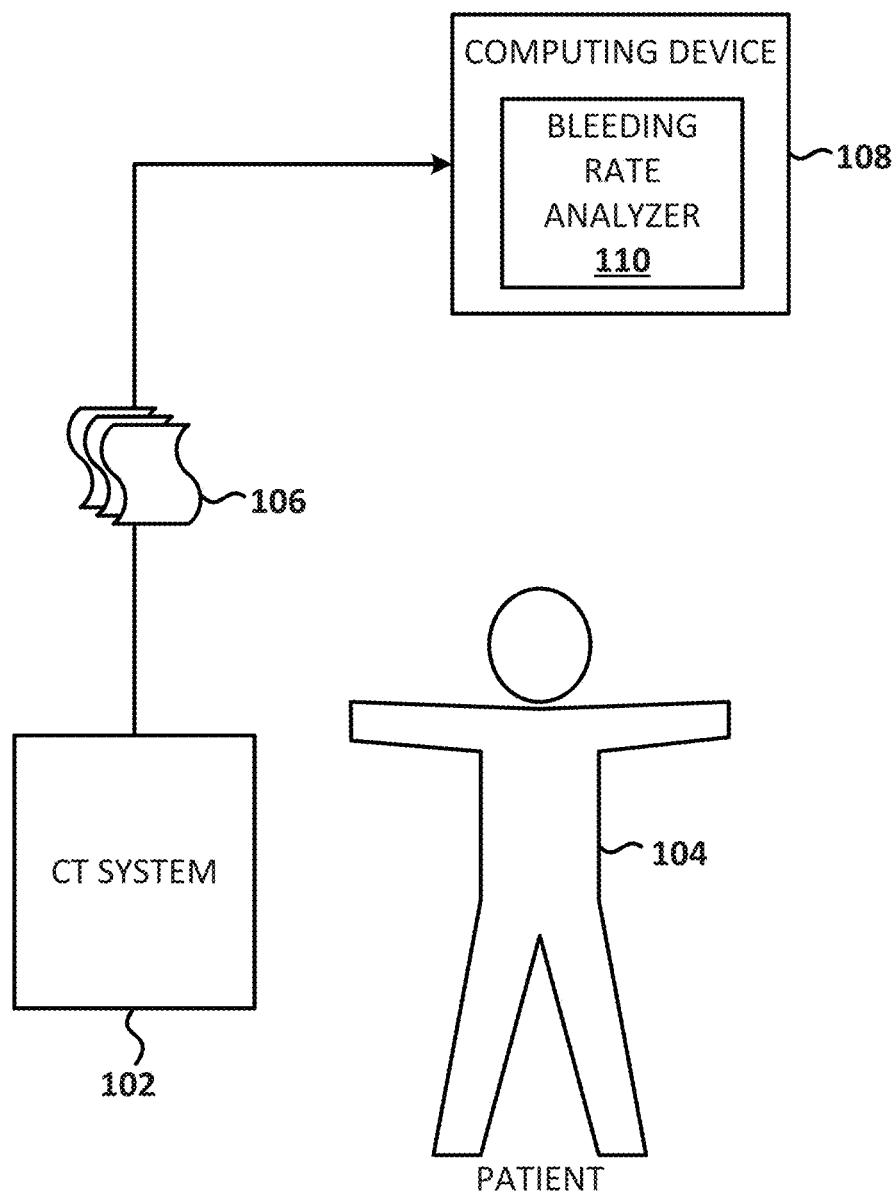
FIG. 1 is a schematic block diagram depicting an illustrative medical environment, in accordance with embodiments of the subject matter disclosed herein.

While the disclosed subject matter is amenable to various modifications and alternative forms, specific embodiments have been shown by way of example in the drawings and are described in detail below. The intention, however, is not to limit the subject matter disclosed herein to the particular embodiments described. On the contrary, the disclosure is intended to cover all modifications, equivalents, and alternatives falling within the scope of the subject matter disclosed herein, and as defined by the appended claims.

DETAILED DESCRIPTION

FIG. 1 is a block diagram depicting an illustrative medical environment 100. The illustrative medical environment 100 includes a computerized tomography (CT) system 102 configured to perform a CT angiography of at least one body region of a human patient 104 to generate CT images 106. According to embodiments, the environment further includes a computing device 108 configured to instantiate a bleeding rate analyzer 110. The computing device 110 may refer to one or more computing devices of any number of different types. In embodiments, the computing device 110 may be integrated with the CT system 102, separate from the CT system 102, and/or the like. The bleeding rate analyzer 110 may be, for example, a computer program configured to analyze CT images to identify active extravasation.

In embodiments, the bleeding rate analyzer 110 may be configured to perform a method of treating a human patient 104 identified as having an injury to a body region. For example, the method may include receiving CT images 106, where the CT images 106 were generated by performing a CT angiography, using a CT system 102, of an injured body region of the human patient 104. The bleeding rate analyzer 110 may be further configured to identify a trigger event, the trigger event including at least one of receiving an input from a clinician and detecting a trigger feature in the CT images 106. The method may further include determining, in response to identifying the trigger event and based on the CT images, a total volumetric rate of active bleeding in the injured body region; and recommending at least one treatment approach for the human patient 104 based on the total volumetric rate of active bleeding.

According to embodiments, the bleeding rate analyzer 110 may be configured, for example, to access a table, database, and/or the like to, determine one or more treatment approaches based on the total volumetric rate of active bleeding. In embodiments, recommending at least one treatment approach comprises displaying, on a display device, an indication of at least one treatment approach. In embodiments, the at least one treatment approach may include embolization, blood transfusion, pelvic packing, pelvic ring stabilization, and/or the like.

According to embodiments, the method may further include providing any number of different types of information related to the analysis. For example, in embodiments, the method may include causing a display device to display a representation (e.g., a number, a graphic, etc.) of the determined total volumetric rate of active bleeding. In embodiments, the method may further include determining and/or displaying a representation of a mortality indicator. For example, in embodiments in which the body region includes the pelvic region, the method may include determining, where the total volumetric rate of active bleeding is less than 20 cc/min, that the human patient has a low risk of mortality; and determining, where the total volumetric rate of active bleeding is more than 20 cc/min, that the human patient has a high risk of mortality. An indicator may be displayed that represents the mortality risk (e.g., a first indicator may represent a low mortality risk while a second indicator may represent a high mortality risk, a variable indicator may represent a variable mortality risk, etc.). According to embodiments, any number of different criteria may be used to determine a risk and any number of different techniques may be used to represent the risk.

The illustrative medical environment 100 shown in FIG. 1 is not intended to suggest any limitation as to the scope of use or functionality of embodiments of the present disclosure. The illustrative environment 100 also should not be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the present disclosure.

Figure 2:
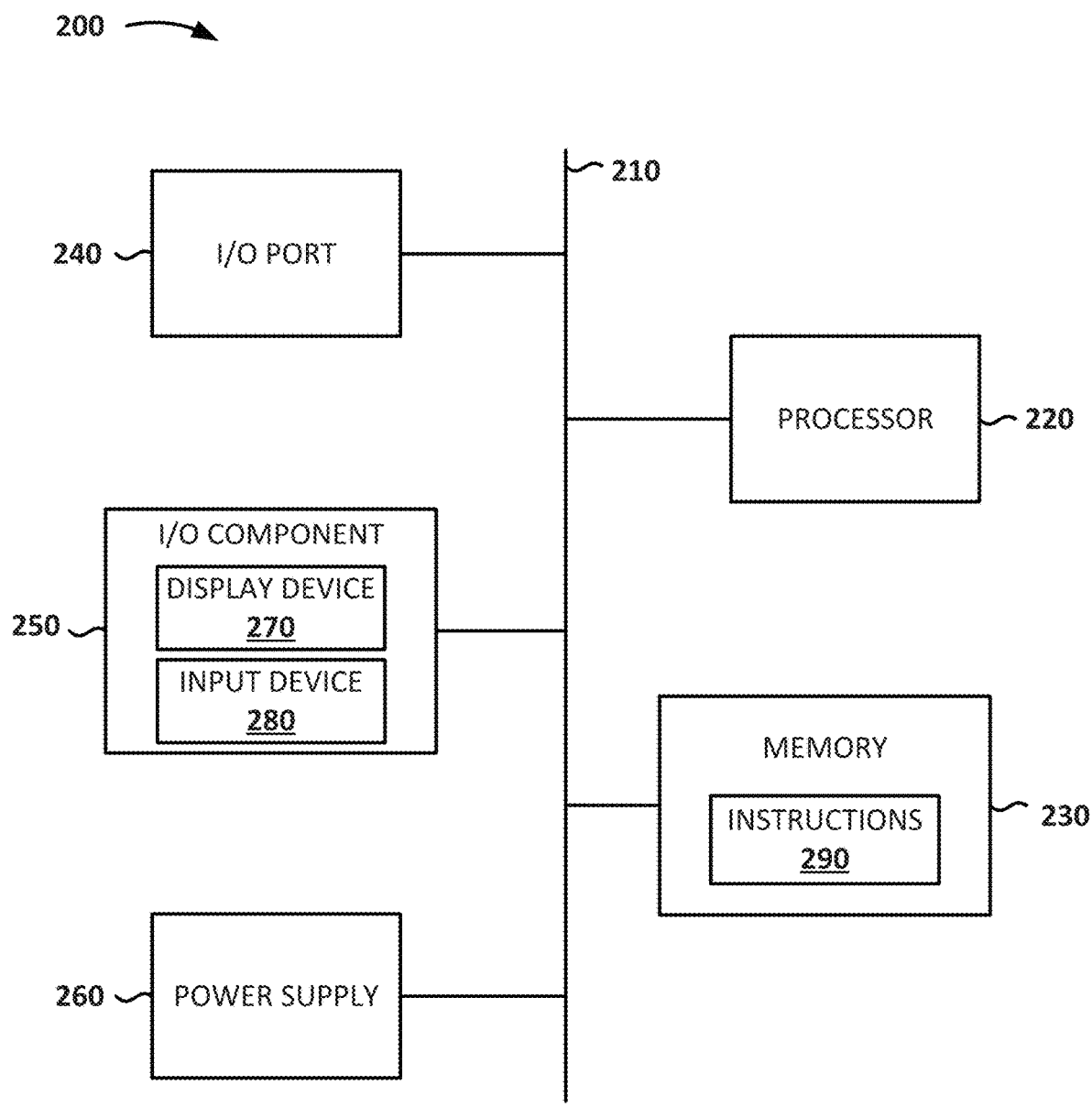
FIG. 2 is a block diagram depicting an illustrative computing device, in accordance with embodiments of the subject matter disclosed herein.

According to various embodiments of the disclosed subject matter, any number of the components depicted in FIG. 1 (e.g., the mobile device 106, the control device 110, etc.)

may be implemented on one or more computing devices. FIG. 2 is a block diagram depicting an illustrative computing device 200, in accordance with embodiments of the disclosure. The computing device 200 may include any type of computing device suitable for implementing aspects of embodiments of the disclosed subject matter. Examples of computing devices include specialized computing devices or general-purpose computing devices such "workstations," "servers," "laptops," "desktops," "tablet computers," "handheld devices," "general-purpose graphics processing units (GPGPUs)," and the like, all of which are contemplated within the scope of FIGS. 1 and 2, with reference to various components of the system 100 and/or computing device 200.

In embodiments, the computing device 200 includes a bus 210 that, directly and/or indirectly, couples the following devices: a processor 220, a memory 230, an input/output (I/O) port 240, an I/O component 250, and a power supply 260. Any number of additional components, different components, and/or combinations of components may also be included in the computing device 200. The I/O component 250 may include a presentation component configured to present information to a user such as, for example, a display device 270, a speaker, a printing device, and/or the like, and/or an input device 280 such as, for example, a microphone, a joystick, a satellite dish, a scanner, a printer, a wireless device, a keyboard, a pen, a voice input device, a touch input device, a touch-screen device, an interactive display device, a mouse, and/or the like.

The bus 210 represents what may be one or more busses (such as, for example, an address bus, data bus, or combination thereof). Similarly, in embodiments, the computing device 200 may include a number of processors 220, a number of memory components 230, a number of I/O ports 240, a number of I/O components 250, and/or a number of power supplies 260. Additionally, any number of these components, or combinations thereof, may be distributed and/or duplicated across a number of computing devices.

In embodiments, the memory 230 includes computer-readable media in the form of volatile and/or nonvolatile memory and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In embodiments, the memory 230 stores computer-executable instructions 290 for causing the processor 220 to implement aspects of embodiments of system components discussed herein and/or to perform aspects of embodiments of methods and procedures discussed herein.

The computer-executable instructions 290 may include, for example, computer code, machine-useable instructions, and the like such as, for example, program components capable of being executed by one or more processors 220 associated with the computing device 200. For example, in embodiments, the computer-executable instructions 290 may be configured to be executed by one or more processors to cause the one or more processors to instantiate the bleeding rate analyzer XXX depicted in FIG. 1. Program components may be programmed using any number of different programming environments, including various languages, development kits, frameworks, and/or the like. Some or all of the functionality contemplated herein may also, or alternatively, be implemented in hardware and/or firmware.

The illustrative computing device 200 shown in FIG. 2 is not intended to suggest any limitation as to the scope of use or functionality of embodiments of the present disclosure. The illustrative computing device 200 also should not be interpreted as having any dependency or requirement related to any single component or combination of components illustrated therein. Additionally, various components depicted in FIG. 2 may be, in embodiments, integrated with various ones of the other components depicted therein (and/or components not illustrated), all of which are considered to be within the ambit of the present disclosure.

Figure 3:
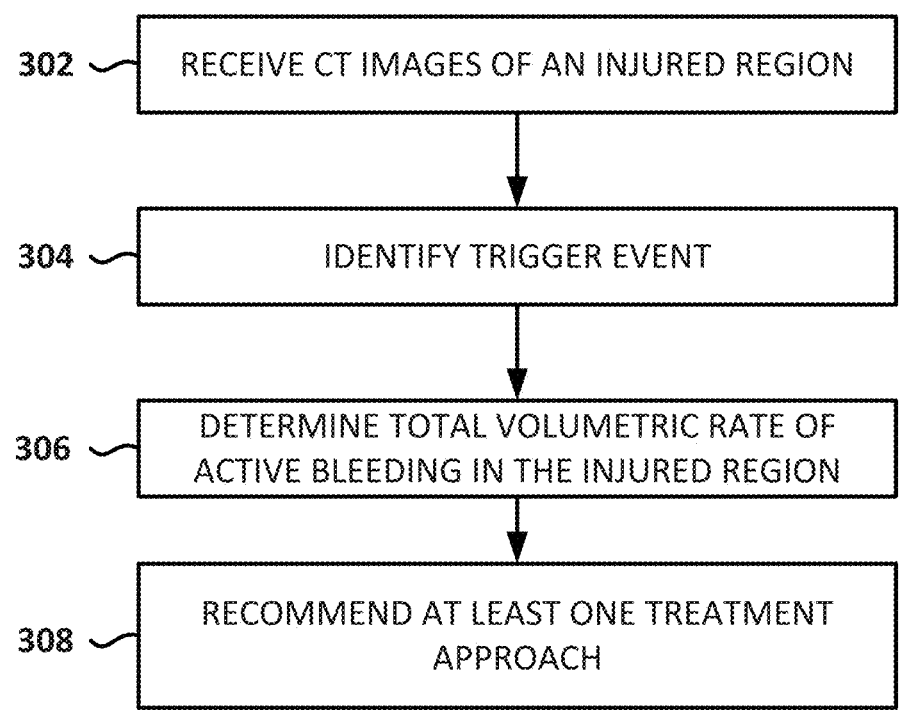
FIG. 3 is a flow diagram depicting an illustrative method of treating a human patient identified as having an injury to a body region, in accordance with embodiments of the subject matter disclosed herein.
Figure 4A:
FIGS. 4A-4D are axial arterial phase and axial parenchymal phase images, in accordance with embodiments of the subject matter disclosed herein.
Figure 4B:
Figure 4C:
Figure 4D:

FIG. 3 is a flow diagram depicting an illustrative method 300 of treating a human patient identified as having an injury to a body region, in accordance with embodiments of the subject matter disclosed herein. According to embodiments, for example, the method may be performed by the bleeding rate analyzer 100 depicted in FIG. 1 and/or as a result of one or more processors 220 executing the instructions 290 depicted in FIG. 2. According to embodiments, the method 300 may include any number of additional and/or alternative steps, consistent with the subject matter disclosed herein.

As shown in FIG. 3, the illustrative method 300 includes receiving CT images (block 302). In embodiments, the CT images are generated by performing a CT angiography of an injured body region of the human patient. In implementations in which the body region includes the pelvic region, the CT images may be generated, for example, by performing a CT angiography of an abdomen and a pelvis of the human patient. In embodiments, the CT images may be provided automatically to the bleeding rate analyzer from the CT system, a storage system, and/or the like.

The illustrative method 300 further includes identifying a trigger event (block 304). According to embodiments, the trigger event may include receiving an input from a clinician, detecting a trigger feature in the CT images, and/or the like. For example, in embodiments, a clinician may use an input device to provide an input to the bleeding rate analyzer to cause the analyzer to perform aspects of the method 300. In embodiments, the bleeding rate analyzer, CT system, and/or other device and/or software may be configured to analyze the CT images to determine whether the CT images include a trigger feature. A trigger feature may include, for example, an aspect of a CT image that represents contrast extravasation, a volume of blood, and/or the like.

In response to identifying the trigger event, the bleeding rate analyzer, CT system, and/or the like may be configured to determine, based on the CT images, a total volumetric rate of active bleeding in the injured body region (block 306). According to embodiments, the determining the total volumetric rate of active bleeding includes determining, based on the CT images, a first local volumetric rate of active bleeding at a first site in the injured body region; determining, based on the CT images, a second local volumetric rate of active bleeding at a second site in the injured body region; and determining, based on the first local volumetric rate and the second volumetric rate, the total volumetric rate of active bleeding. In embodiments, the total volumetric rate of active bleeding may be determined based on any number of local volumetric rates. That is, for example, the total volumetric rate of active bleeding may be determined based on three, four, five, six, seven, eight, nine, ten, or any other number of local volumetric rates. According to embodiments, determining the total volumetric rate of active bleeding includes summing the local volumetric rates of active bleeding, determining an average volumetric rate based on the local volumetric rates of active bleeding, applying a mathematical model based on the local volumetric rates, and/or the like.

In embodiments, determining the first local volumetric rate of active bleeding may include, for example, determining, based on the CT images, a first volume, the first volume comprising a volume of active extravasation at the first site on an arterial phase; determining, based on the CT images, a second volume, the second volume comprising a volume of active extravasation at the first site on a parenchymal phase; subtracting the first volume from the second volume to determine a first local active bleeding volume; and dividing the first local active bleeding volume by an amount of time between the arterial phase and the parenchymal phase. Similarly, determining the second local volumetric rate of active bleeding includes determining, based on the CT images, a third volume, the third volume comprising a volume of active extravasation at the second site on an arterial phase; determining, based on the CT images, a fourth volume, the fourth volume comprising a volume of active extravasation at the second site on a parenchymal phase; subtracting the third volume from the fourth volume to determine a second local active bleeding volume; and dividing the second local active bleeding volume by an amount of time between the arterial phase and the parenchymal phase.

As is further shown in FIG. 3, the illustrative method 300 further includes recommending at least one treatment approach for the human patient based on the total volumetric rate of active bleeding (block 308). According to embodiments, the bleeding rate analyzer may be configured, for example, to access a table, database, and/or the like to, determine one or more treatment approaches based on the total volumetric rate of active bleeding. In embodiments, recommending at least one treatment approach comprises displaying, on a display device, an indication of at least one treatment approach. In embodiments, the at least one treatment approach may include embolization, blood transfusion, pelvic packing, pelvic ring stabilization, and/or the like.

According to embodiments, the illustrative method may further include providing any number of different types of information related to the analysis. For example, in embodiments, the illustrative method may include causing a display device to display a representation (e.g., a number, a graphic, etc.) of the determined total volumetric rate of active bleeding. In embodiments, the illustrative method may further include determining and/or displaying a representation of a mortality indicator. For example, in embodiments in which the body region includes the pelvic region, the method may include determining, where the total volumetric rate of active bleeding is less than 20 cc/min, that the human patient has a low risk of mortality; and determining, where the total volumetric rate of active bleeding is more than 20 cc/min, that the human patient has a high risk of mortality. An indicator may be displayed that represents the mortality risk (e.g., a first indicator may represent a low mortality risk while a second indicator may represent a high mortality risk, a variable indicator may represent a variable mortality risk, etc.). According to embodiments, any number of different criteria may be used to determine a risk and any number of different techniques may be used to represent the risk.

Experimental Data

This was a retrospective cohort study which included 29 patients from a 4-year period (May 2013 to May 2017). Patients with acute pelvic fractures and active bleeding detected on CT with two phases of imaging were included. Software was used to measure the volume of active bleeding on arterial and parenchymal phases. The active bleeding rate was calculated by dividing the change in active bleeding volume by the time between the two phases. The total volumetric bleed rate from all sites was then computed.

The Radiology Information System (RIS) and Trauma Registry was searched for patients who were at least 18 years of age with acute pelvic fractures and active bleeding detected on dual phase (arterial and parenchymal phases) CT during a 4-year period (May 2013 to May 2017). Any patients who died prior to imaging were excluded, as well as patients who did not have an active source of bleeding originating in the pelvis. The following anatomic regions were defined, for the study, for denoting the location of active bleeding: pelvis, thigh, gluteal, and retroperitoneum. The pelvic region was defined by the following borders: iliac crests and greater trochanters laterally, ischial tuberosities inferiorly, and the top of the iliac crests superiorly. Bleeding into the thigh region included areas external to the pelvic ring, anterior to the greater trochanters and down to the proximal thigh included as a part of the scan (inferior border). The gluteal region was defined as the space external to the pelvic ring, posterior to the anterior border of the greater trochanter and down to the proximal thigh included as a part of the scan (inferior border). Lastly, the retroperitoneum included hematoma originating from a pelvic fracture extending into the retroperitoneal space above the iliac crests.

The mean age was 52 (range 18 to 87 years) and 22 (75.9%) were male. The three most common mechanisms of injury were motor vehicle collisions (MVC), pedestrians struck by a motor vehicle, and motorcycle accidents. Characteristics of the 29 study patients are shown in Table 1:

TABLE 1

| Characteristic | No. of Patients |
| --- | --- |
| Male sex | 22 |
| Age (years) | |
| 15-44 | 11 |
| 45-64 | 9 |
| ≥60 | 9 |
| Systolic blood pressure <90 mmHg on admission | 5 |
| pRBC transfusion | 23 |
| ≥4 units | 17 |
| <4 units | 12 |
| Mechanism of injury (%) | |
| MVC | 9 (31) |
| Motorcycle | 7 (24) |
| Pedestrian vs. vehicle | 6 (21) |
| Fall from height | 2 (7) |
| Crush accident | 3 (10) |
| Moped | 1 (3) |
| ATV | 1 (3) |
| Angiogram performed | 15 |

Dual-phase CT of the abdomen and pelvis was examined for additional sites of active bleeding outside the pelvis. Additional sites of bleeding within the abdomen were included in the analysis.

One of ordinary skill in the art recognizes that commercially available software packages may be used to generate three-dimensional volumetric measurements to measure the size of active bleeding on more than one phase. An example of a commercially available software package that uses semi-automated technology is Philips IntelliSpace Portal, Best, The Netherlands. Other software packages to generate 3D volumetric measurements to measure the size of active bleeding on more than one phrase may also be used.

The size of active bleeding was measured for all observed sites on the CT of the abdomen and pelvis. An electronic cursor was used to trace the volume of active extravasation on each slice of the CT for both the arterial and parenchymal phases of the scan. The software takes into account the thickness of the slice being measured and sums the volume of measured extravasation from each slice. The software is then able to calculate the volume. Measurements were made by a board-certified radiologist who is fellowship trained in trauma/emergency radiology. FIGS. 4A-4D illustrate axial arterial phase images with (FIG. 4A) and without (FIG. 4B) measurement of the active extravasation volume and axial parenchymal phase images with (FIG. 4C) and without (FIG. 4D) measurement of the active extravasation volume. The arterial phase volume was 2.9 ml and the parenchymal phase volume was 7.4 ml. There were 32 s between the arterial and parenchymal phase images. The bleed rate is determined as follows. (Bleed Rate=(7.4 ml−2.9 ml)/32 s)=0.141 ml/s=8.4 ml/mins.

The active bleeding rate was calculated by dividing the change in active bleeding focus volume by the time between the arterial and parenchymal phases. For patients with multiple sites of active bleeding, the rate of active bleeding was calculated at each individual site and subsequently summed to determine the total rate of active bleeding. If patients had additional sites of active bleeding within the abdomen, then these sites were included in the total active bleeding rate. In addition to measuring active extravasation, pelvic hematoma volumes were measured on the parenchymal phase scans for all study patients.

Clinical variables were compared between survivors and non-survivors. In addition, clinical variables were examined for associations with the total bleed rate and pelvic hematoma volume. The following clinical variables were obtained from the trauma registry for each patient: systolic blood pressure (SBP) on admission, diastolic blood pressure on admission, heart rate on admission, unassisted respiratory rate, oxygen saturation on admission, units of blood transfused, intervention (embolization, blood transfusion, pelvic packing, pelvic ring stabilization, laparotomy), hematocrit level, length of stay (LOS), ICU length of stay (ICU LOS), injury severity score (ISS), trauma and injury severity score (TRISS), abbreviated injury scale (AIS) score, and final disposition (survival, death). Pelvic fractures were classified using the Young-Burgess classification system.

For patients whose pelvic fracture did not fall into the classification system, the specific fracture was recorded.

The data was checked for normality using the Shapiro-Wilk test. If the data was normally distributed, an independent samples t test was used to compare clinical variables between survivors and non-survivors. Otherwise, the Mann-Whitney U test was used on data that was not normally distributed. Cross tabulation using the X2 statistic was used to check for associations between categorical variables. The Pearson product-moment correlation coefficient was used to measure the strength and direction of association between clinical variables that were normally distributed while Spearman's rank correlation coefficient was used on data that was not normally distributed. Risk ratios were calculated for mortality, arterial injury on angiogram, and transfusion requirements exceeding 6 units of packed red blood cells (pRBCs). All data analysis was performed using SPSS (IBM Corp. Released 2016. IBM SPSS Statistics for Windows, Version 24.0. Armonk, N.Y.: IBM Corp).

Figure 5:
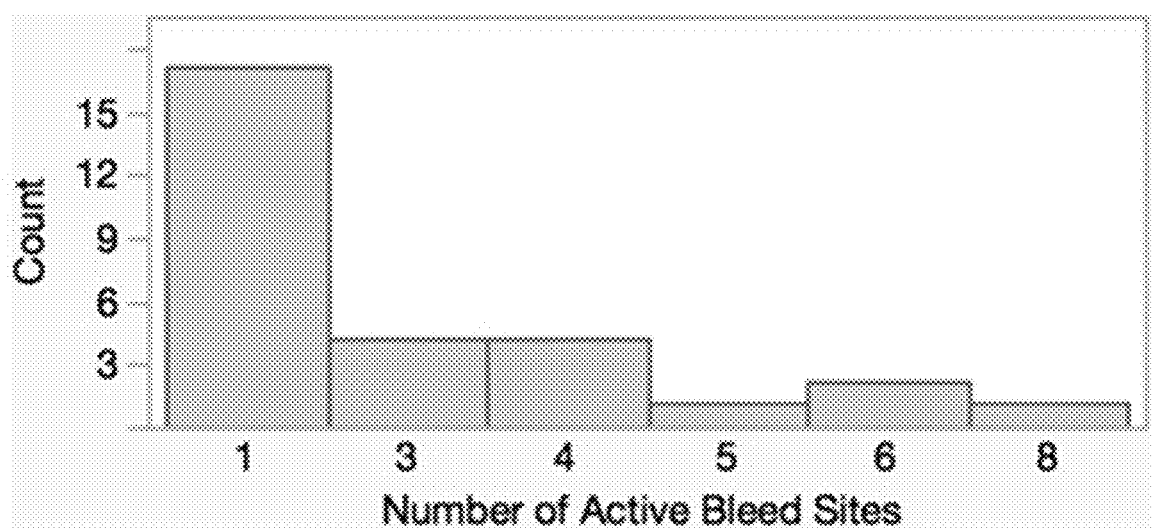
FIG. 5 is a histogram showing the total number of active bleed sites for each patient, in accordance with embodiments of the subject matter disclosed herein.

As shown in FIG. 5, most patients only had one site of active bleeding (n=17, 59%), although one patient had eight sites of active bleeding.

Table 2 shows the distribution of the delay time between the arterial and parenchymal phases for measurement of active extravasation volumes. As shown in Table 2, the mean time between arterial and parenchymal phases was approximately 49 s (range 28 to 107 s). The distribution roughly fell into two groups: 30-35 s and 60-90 s. The more delayed parenchymal phases were obtained if the patient underwent whole body CTA to include the lower extremities. The additional lower extremity scan time and table realignment contributed to the prolonged scan time. The volume of active extravasation of contrast always increased when going from the arterial to the parenchymal phase.

TABLE 2

| Time difference between arterial and parenchymal phases (minutes:seconds) | Number of cases |
| --- | --- |
| <00:30 | 1 |
| 00:30-00:45 | 43 |
| >00:45-1:00 | 7 |
| >1:00-1:30 | 17 |
| >1:30 | 4 |

Figure 6:
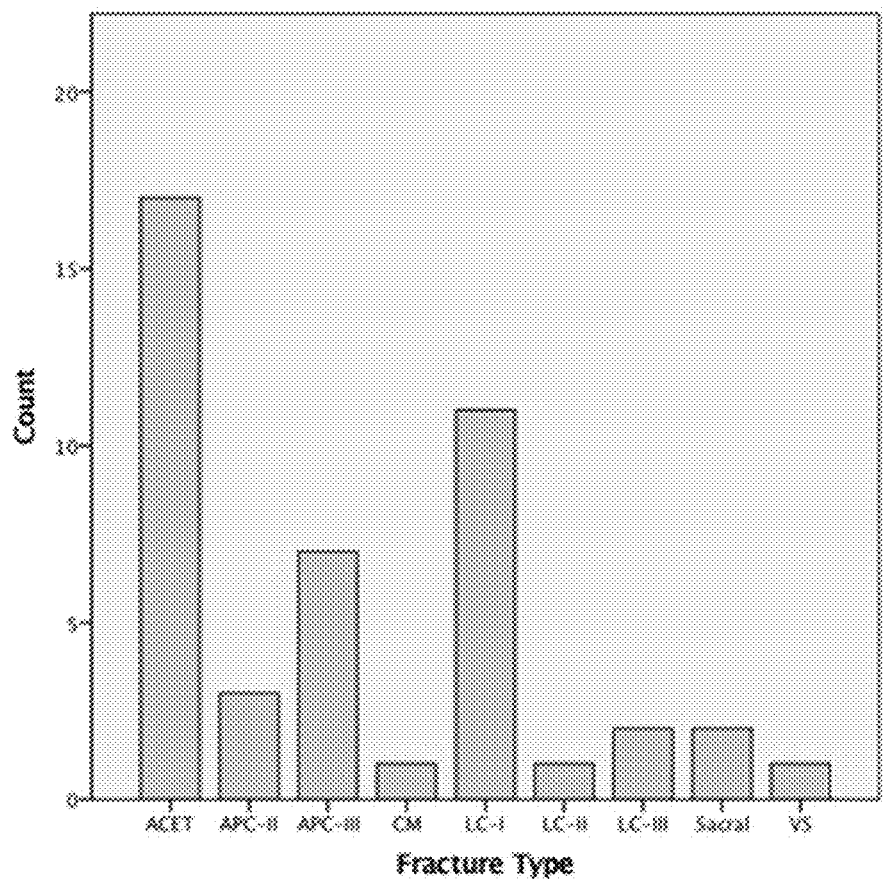
FIG. 6 is a histogram showing the pelvic fracture type classification using the Young and Burgess classification system, in accordance with embodiments of the subject matter disclosed herein.

Overall mortality for the group was 21% (n=6), which is slightly above that observed in prior studies. Seventy-nine percent (79%, n=23) of patients had an intervention such as angiography (n=15), exploratory laparotomy (n=5), open reduction internal fixation of pelvic fracture (n=15), or closed reduction external fixation of pelvic fracture (n=8). Fifty-two percent (n=15) of the study patients underwent angiography. Of those human patients who underwent angiography, 80% (n=12) had active contrast extravasation and underwent embolization. A total of 14 patients (48%) received at least 4 units of pRBCs (FIG. 6).

Figure 7:
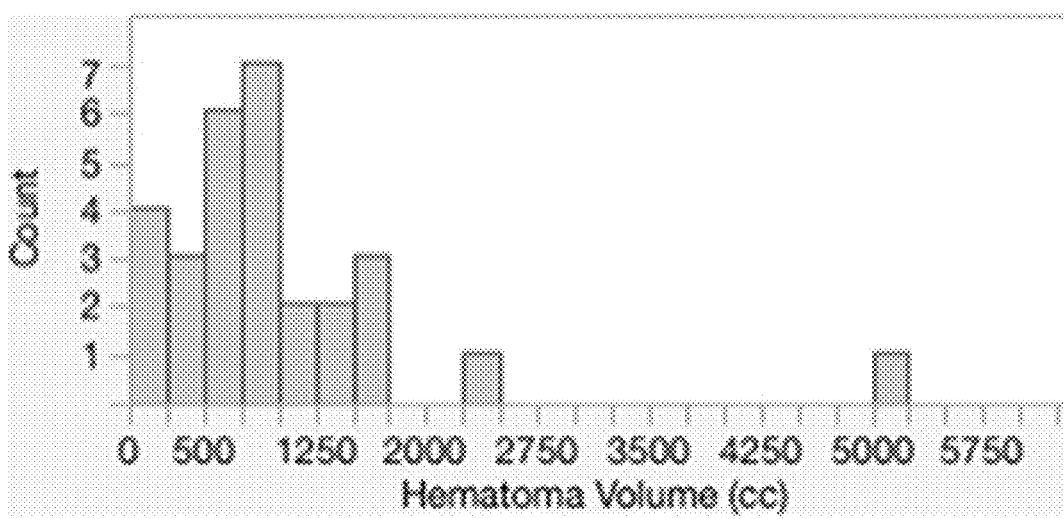
FIG. 7 is a histogram showing the distribution of pelvic hematoma volumes for the cohort, in accordance with embodiments of the subject matter disclosed herein.

The mean abdominopelvic bleed rate for the cohort was 13.0 cc/min (range 0.1 to 143.2 cc/min). The mean pelvic hematoma volume for all sites was 975.1 cc (range 82.2 to 5122.7 cc). FIG. 7 shows the distribution of pelvic hematoma volumes for the cohort. The mean abdominopelvic volumetric bleed rate was significantly higher in the non-survivors compared to the survivors (40.7 cc/min vs. 5.7 cc/min, respectively; p<0.01). One outlier was present with a bleed rate of 143.2 cc/min. This patient had an ATV accident that resulted in multiple pelvic fractures and underwent embolization of the bilateral internal iliac, superior gluteal, left inferior gluteal, and right common iliac arteries. When excluding this outlier, a statistically significant difference still exists between abdominopelvic bleed rates in survivors and non-survivors (p=0.03).

Figure 8:
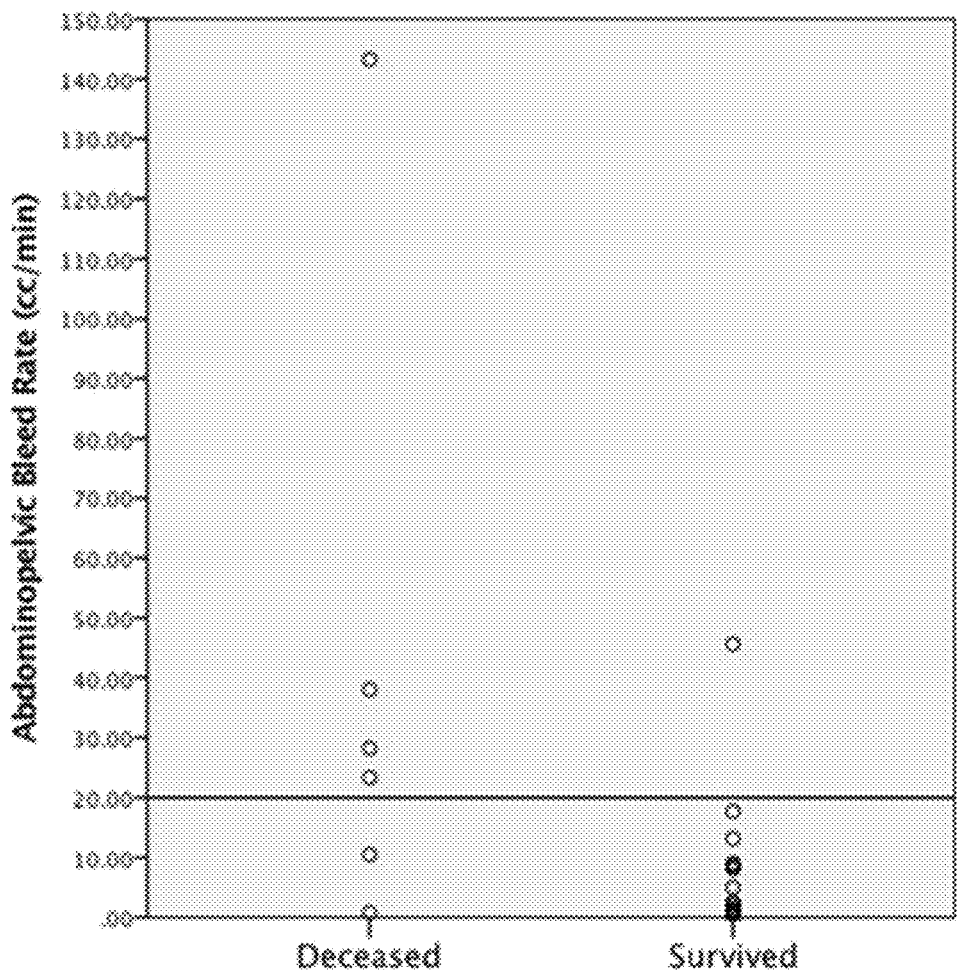
FIG. 8 is a plot showing the mean abdominopelvic bleed rates for both the survivors and non-survivors.

FIG. 8 shows a plot of the mean abdominopelvic bleed rates for both the survivors and non-survivors. Ninety-six percent (96%) of patients in the survival group had an abdominopelvic bleed rate less than 20 cc/min compared to 33% of non-survivors.

Table 3 is a comparison of clinical outcomes and patient characteristics between the survivors and non-survivors.

TABLE 3

| Clinical Variable | Survivors (mean) | Non-survivors (mean) | p value |
| --- | --- | --- | --- |
| Age (years) | 50.3 | 58.8 | 0.34 |
| ISS | 31.0 | 61.3 | <0.01 |
| Hospital LOS (days) | 16.0 | 1.0 | <0.01 |
| ICU LOS (days) | 7.9 | 1.0 | <0.01 |
| Abdominopelvic bleed rate (cc/min) | 5.7 | 40.7 | <0.01 |

TABLE 3-continued

| Clinical Variable | Survivors (mean) | Non-survivors (mean) | p value |
|---|---|---|---|
| Pelvic bleed rate (cc/min) | 5.4 | 35.8 | 0.02 |
| Number of pelvic fractures | 1.6 | 1.5 | 0.79 |
| Number of active bleeding foci | 2.0 | 3.8 | 0.02 |
| Hematoma volume (cc) | 745.8 | 1853.9 | <0.01 |
| Units of pRBC transfused (mean) | 7.7 | 14.7 | 0.10 |
| SBP on admission (mmHg) | 120.6 | 101.7 | 0.15 |

An abdominopelvic bleed rate >20 cc/min was associated with a mortality rate of 80% while a rate of <20 cc/min was associated with a 92% survival rate (Table 3). The mean pelvic hematoma volume was much greater in the non-survivors compared to the survivors (1853.9 cc vs. 745.8 cc, respectively; p<0.01). The mean hospital LOS and ICU LOS were significantly greater in the survivors (Table 3). The non-survivors received twice as many pRBC transfusions as the survivors (mean 14.7 U pRBC vs. 7.7 U pRBC, respectively), but this was not statistically significant (p=0.1). Analysis was also performed while excluding the extrapelvic sites of active bleeding and using only the active bleeding rate into the pelvis. Overall, the mean pelvic bleed rate was 11.7 cc/min (range 0.1 to 142.9 cc/min). The mean pelvic bleed rates in the non-survivors and survivors were 35.8 cc/min and 5.4 cc/min, respectively (p=0.02).

Sites of active bleeding (pelvic, gluteal, thigh, and retroperitoneal) were compared between survivors and non-survivors. There was no statistically significant association between the site of active bleeding and mortality (p=0.27). Conversely, there was a statistically significant difference in outcome when comparing number of bleed sites between survivors and non-survivors which ranged from one site to eight (p=0.02). FIG. 5 shows the distribution of number of bleed sites for the cohort. The mean number of pelvic fractures ranged from one to three, but there was no statistically significant difference between the number of fractures in the survivors and non-survivors groups (p=0.79). Lastly, when patients were placed into groups based on the Young-Burgess classification of the pelvic fracture, there was no association between fracture pattern and mortality (p=0.22). FIG. 3 shows a distribution of the fracture patterns for the cohort.

The mean ISS of the survivors and non-survivors was 31 and 61, respectively. This difference was statistically significant (p<0.01). When comparing the ISS for patients with abdominopelvic bleed rates above 20 cc/min and below 20 cc/min, there was a statistically significant difference in the ISS of 33.8 and 54.0, respectively (p=0.01). Statistically significant associations were also seen between the ISS and pelvic hematoma volume (rs=0.37, n=29, p=0.04) and the ISS and abdominopelvic bleed rate (rs=0.51, n=29, p<0.01).

TRISS scores were obtained for 23 of the patients and the mean score was 0.847 (range 0.351 to 0.987). Four patients from the mortality group and two from the survivors did not have TRISS scores as these patients were intubated and the unassisted respiratory rate is needed for calculation of the TRISS score. Based on the mean TRISS score for the subset of the cohort with TRISS scores, predicted mortality was estimated to be approximately 15.3% while the actual mortality was 12%. There was a statistically significant difference between the mean TRISS score of the survivors and non-survivors group (p=0.02).

A Spearman's correlation was run to determine the relationship between the total rate of abdominopelvic bleeding and pelvic hematoma volume. There was a strong, positive correlation between the total rate of bleeding and pelvic hematoma volume (rs=0.55, n=29, p<0.01). A positive correlation was observed between the pelvic hematoma volume and the total number of units of pRBC transfused (rs=0.40, n=29, p=0.03), but no correlation was observed between abdominopelvic bleed rate and total units pRBC transfused (rs=0.37, n=29, p=0.06). Lastly, there was no correlation between SBP on admission and abdominopelvic bleed rate (r−s=−0.36, n=29, p=0.05) or SBP on admission and pelvic hematoma volume (r=−0.26, n=29, p=0.17).

Of the 15 patients who underwent angiography, 12 had active arterial contrast extravasation and underwent embolization. There was no statistically significant difference between the mean pelvic hematoma volumes in patients who underwent arterial embolization compared to those who did not require embolization (1284.8 cc vs. 889.1 cc, respectively; p=0.62). Similarly, there was no difference in the mean abdominopelvic rate of bleeding in patients who underwent embolization compared to those who did not undergo the procedure (20.4 cc vs. 21.6 cc, respectively; p=0.56).

The risk ratio for arterial injury for pelvic hematoma volumes over 500 cc was 1.69, but was not statistically significant (p=0.37, 95% CI 0.42 to 6.90). Similarly, the relative risk for a transfusion requirement of 6 or more units of pRBCs for pelvic hematoma volumes over 500 cc was not statistically significant and was 1.91 (p=0.39, 95% CI 0.56 to 6.54). Lastly, the relative risk of death for patients with a pelvic hematoma volume greater than 500 cc was 0.73 (p=0.29, 95% CI 0.56 to 0.94) and was not statistically significant.

A strong association between both the abdominopelvic bleeding rate and pelvic hematoma volume with mortality from the initial trauma was observed. Active contrast extravasation on CT was also a strong predictor of arterial injury as 80% of patients who showed contrast extravasation on CT showed contrast extravasation on catheter angiography and subsequently underwent embolization.

A statistically significant difference was found between the TRISS scores of the non-survivors and the survivors (p=0.02). The predicted mortality based on TRISS score and actual mortality were similar with rates of 15% and 12%, respectively. An actual mortality rate greater than that predicted by the TRISS score would further support additional factors such as the rate of active bleeding in predicting mortality for pelvic fracture patients.

A positive correlation between pelvic hematoma size and abdominopelvic bleed rate was found (rs=0.55, n=29, p<0.01). Also, the hematoma volume was larger in non-survivors (p<0.01), but the bleed rate was higher as well (p<0.01).

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A method for operating a computing system including at least one processor to determine a treatment for a human patient identified as having an injury to a body region, comprising:

receiving, by the at least one processor, CT images, wherein the CT images were generated by performing a CT angiography of an injured body region of the human patient;

detecting, by the at least one processor based on the CT images, a trigger feature in the CT images, and automatically, in response to the detection of the trigger feature, determining, by the at least one processor based on the CT images, a total volumetric rate of active bleeding in the injured body region to an accuracy of at least 0.1 cc/min, comprising:

determining, by the at least one processor based on the CT images, a first local volumetric rate of active bleeding at a first site in the injured body region to an accuracy of at least 0.1 cc/min, wherein the determination is made by:

determining a first volume of extravasation at the first site during a first imaging phase;

determining a second volume of extravasation at the first site during a second imaging phase; and determining the first local volumetric rate of active bleeding at the first site based upon the first volume of extravasation and the second volume of extravasation at the first site and an amount of time between the first and second imaging phases at the first site;

determining, by the at least one processor based on the CT images, a second local volumetric rate of active bleeding at a second site in the injured body region to an accuracy of at least 0.1 cc/min, wherein the determination is made by:

determining a third volume of extravasation at the second site during a first imaging phase;

determining a fourth volume of extravasation at the second site during a second imaging phase; and determining the second local volumetric rate of active bleeding at the second site based upon the third volume of extravasation and the fourth volume of extravasation at the second site and an amount of time between the first and second imaging phases at the second site; and determining, by the at least one processor based on the first local volumetric rate and the second volumetric rate, the total volumetric rate of active bleeding; and recommending, by the at least one processor, at least one treatment approach for the human patient based on the total volumetric rate of active bleeding.

2. The method of claim 1, wherein determining the first local volumetric rate of active bleeding comprises, by the at least one processor:

determining, based on the CT images, the first volume of active extravasation at the first site on an arterial phase;

determining, based on the CT images, the second volume of active extravasation at the first site on a parenchymal phase;

subtracting the first volume from the second volume to determine a first local active bleeding volume; and dividing the first local active bleeding volume by an amount of time between the arterial phase and the parenchymal phase.

3. The method of claim 2, wherein determining the second local volumetric rate of active bleeding comprises, by the at least one processor:

determining, based on the CT images, the third volume of active extravasation at the second site on an arterial phase;

determining, based on the CT images, the fourth volume of active extravasation at the second site on a parenchymal phase;

subtracting the third volume from the fourth volume to determine a second local active bleeding volume; and dividing the second local active bleeding volume by an amount of time between the arterial phase and the parenchymal phase.

4. The method of claim 3, wherein determining the total volumetric rate of active bleeding comprises, by the at least one processor, at least one of summing the first and second local volumetric rates of active bleeding and determining an average volumetric rate based on the first and second local volumetric rates of active bleeding.

5. The method of claim 1, wherein the body region comprises the pelvic region.

6. The method of claim 5, further comprising, by the at least one processor:

determining, where the total volumetric rate of active bleeding is less than 20 cc/min, that the human patient has a low risk of mortality; and determining, where the total volumetric rate of active bleeding is more than 20 cc/min, that the human patient has a high risk of mortality.

7. The method of claim 1, wherein recommending at least one treatment approach comprises, by the at least one processor, displaying, on a display device, an indication of at least one treatment approach.

8. The method of claim 1, wherein the at least one treatment approach comprises at least one of embolization, blood transfusion, pelvic packing, and pelvic ring stabilization.

9. A method for operating a computing system including at least one processor to determine a treatment for a human patient identified as having a pelvic injury, the method comprising:

receiving, by the at least one processor, CT images, wherein the CT images were generated by performing a CT angiography of an abdomen and a pelvis of the human patient;

detecting, by the at least one processor based on the CT images, a trigger feature in the CT images, and automatically, in response to the detection of the trigger feature, determining by the at least one processor, based on the CT images, a total volumetric rate of active abdominopelvic bleeding to an accuracy of at least 0.1 cc/min, comprising:

determining by the at least one processor, based on the CT images, a first local volumetric rate of active bleeding at a first site in the injured body region to an accuracy of at least 0.1 cc/min, wherein the determination is made by:

determining a first volume of extravasation at the first site during a first imaging phase;

determining a second volume of extravasation at the first site during a second imaging phase; and determining the first local volumetric rate of active bleeding at the first site based upon the first volume of extravasation and the second volume of extravasation at the first site and an amount of time between the first and second imaging phases at the first site;

determining by the at least one processor, based on the CT images, a second local volumetric rate of active bleeding at a second site in the injured body region to an accuracy of at least 0.1 cc/min, wherein the determination is made by:
  determining a third volume of extravasation at the second site during a first imaging phase;
  determining a fourth volume of extravasation at the second site during a second imaging phase; and
  determining the second local volumetric rate of active bleeding at the second site based upon the third volume of extravasation and the fourth volume of extravasation at the second site and an amount of time between the first and second imaging phases at the second site; and
determining by the at least one processor, based on the first local volumetric rate and the second volumetric rate, the total volumetric rate of active bleeding; and
recommending, by the at least one processor, at least one treatment approach for the human patient based on the total volumetric rate of active abdominopelvic bleeding.

10. The method of claim 9, further comprising, by the at least one processor:
  determining, where the total volumetric rate of active abdominopelvic bleeding is less than 20 cc/min, that the human patient has a low risk of mortality; and
  determining, where the total volumetric rate of active abdominopelvic bleeding is more than 20 cc/min, that the human patient has a high risk of mortality.

11. The method of claim 9, wherein recommending at least one treatment approach comprises, by the at least one processor, displaying, on a display device, an indication of at least one treatment approach, the at least one treatment approach comprising at least one of embolization, blood transfusion, pelvic packing, and pelvic ring stabilization.

12. One or more non-transitory computer-readable media having embodied thereon computer-executable instructions that, when executed by a processor, cause the processor to determine a treatment for a human patient identified as having an injury to a body region by:
  receiving CT images, wherein the CT images were generated by performing a CT angiography of an injured body region of the human patient;
  identifying a trigger event based on the CT images, the trigger event comprising detecting a trigger feature in the CT images;
  determining automatically in response to identifying the trigger event and based on the CT images, a total volumetric rate of active bleeding in the injured body region to an accuracy of at least 0.1 cc/min comprising:
    determining based on the CT images, a first local volumetric rate of active bleeding at a first site in the injured body region to an accuracy of at least 0.1 cc/min, wherein the determination is made by:
      determining a first volume of extravasation at the first site during a first imaging phase;
      determining a second volume of extravasation at the first site during a second imaging phase; and
      determining the first local volumetric rate of active bleeding at the first site based upon the first volume of extravasation and the second volume of extravasation at the first site and an amount of time between the first and second imaging at the first site;
    determining, based on the CT images, a second local volumetric rate of active bleeding at a second site in the injured body region to an accuracy of at 0.1 cc/min, wherein the determination is made by:
      determining a third volume of extravasation at the second site during a first imaging phase;
      determining a fourth volume of extravasation at the second site during a second imaging phase; and
      determining the second local volumetric rate of active bleeding at the second site based upon the third volume of extravasation and the fourth volume of extravasation at the second site and an amount of time between the first and second imaging phases at the second site; and
  determining, based on a first local volumetric rate and the second volumetric rate, the total volumetric rate of active bleeding; and
  recommending at least one treatment approach for the human patient based on the total volumetric rate of bleeding.

13. The media of claim 12, wherein the instructions cause the processor to determine the first local volumetric rate of active bleeding by:
  determining, based on the CT images, the first volume of active extravasation at the first site on an arterial phase;
  determining, based on the CT images, the second volume of active extravasation at the first site on a parenchymal phase;
  subtracting the first volume from the second volume to determine a first local active bleeding volume; and
  dividing the first local active bleeding volume by an amount of time between the arterial phase and the parenchymal phase.

14. The media of claim 12, wherein the body region comprises the pelvic region.

15. The media of claim 12, further comprising instructions that cause the processor to recommend the at least one treatment approach by:
  determining, where the total volumetric rate of active bleeding is less than 20 cc/min, that the human patient has a low risk of mortality; and
  determining, where the total volumetric rate of active bleeding is more than 20 cc/min, that the human patient has a high risk of mortality.

16. The media of claim 12, wherein the instructions cause recommending at least one treatment approach by causing a display device to display an indication of at least one treatment approach, the at least one treatment approach comprising at least one of embolization, blood transfusion, pelvic packing, and pelvic ring stabilization.

17. A method for operating a computing system including at least one processor to determine a treatment for a human patient identified as having an injury to a body region, comprising:
  receiving CT images by the at least one processor, wherein the CT images were generated by performing a CT angiography of an injured body region of the human patient;
  detecting, by the at least one processor based on the CT images, a trigger feature in the CT images, and automatically, in response to the detection of the trigger feature, determining, by the at least one processor based on the CT images, a total volumetric rate of active bleeding in the injured body region to an accuracy of at least 0.1 cc/min, wherein the determination is made by:
    determining a first volume of extravasation during a first imaging phase;
    determining a second volume of extravasation during a second imaging phase; and determining the total volumetric rate of active bleeding based upon the first volume of extravasation and the second volume of extravasation and an amount of time between the first and second imaging phases; and recommending, by the at least one processor, at least one treatment approach for the human patient based on the total volumetric rate of active bleeding, wherein the at least one treatment approach comprises at least one of embolization, blood transfusion, pelvic packing, and pelvic ring stabilization.

18. The method of claim 17, further comprising, by the at least one processor, displaying, on a display device, the indication of the at least one treatment approach.

19. A method for operating a computing system including at least one processor to determine a treatment for a human patient identified as having a pelvic injury, the method comprising:

receiving CT images by the at least one processor, wherein the CT images were generated by performing a CT angiography of an abdomen and a pelvis of the human patient;

detecting, by the at least one processor based on the CT images, a trigger feature in the CT images, and automatically, in response to the detection of the trigger feature, determining by the at least one processor, based on the CT images, a total volumetric rate of active abdominopelvic bleeding to an accuracy of at least 0.1 cc/min, wherein the determination is made by:

determining a first volume of extravasation during a first imaging phase;

determining a second volume of extravasation during a second imaging phase; and determining the total volumetric rate of active bleeding based upon the first volume of extravasation and the second volume of extravasation and an amount of time between the first and second imaging phases; and recommending, by the at least one processor, at least one treatment approach for the human patient based on the total volumetric rate of active abdominopelvic bleeding;

determining by the at least one processor, where the total volumetric rate of active abdominopelvic bleeding is less than 20 cc/min, that the human patient has a low risk of mortality; and determining by the at least one processor, where the total volumetric rate of active abdominopelvic bleeding is more than 20 cc/min, that the human patient has a high risk of mortality.

* * * * *